(12) United States Patent
Bidarian Moniri

(10) Patent No.: US 11,957,840 B2
(45) Date of Patent: Apr. 16, 2024

(54) DEVICE FOR SPEECH THERAPY, ADMINISTRATION OF INHALATION MEDICATION AND FOR TREATMENT OF OTITIS, SINUSITIS AND BAROTRAUMA

(71) Applicant: Armin Bidarian Moniri, Portimão (PT)

(72) Inventor: Armin Bidarian Moniri, Portimão (PT)

( * ) Notice: Subject to any disclaimer, the term of this patent is extended or adjusted under 35 U.S.C. 154(b) by 623 days.

(21) Appl. No.: 17/167,362

(22) Filed: Feb. 4, 2021

(65) Prior Publication Data

US 2021/0154425 A1 May 27, 2021

Related U.S. Application Data

(63) Continuation of application No. PCT/PT2019/050028, filed on Aug. 9, 2019.

(60) Provisional application No. 62/716,542, filed on Aug. 9, 2018.

(51) Int. Cl.
*A61M 16/06* (2006.01)
*A61M 16/08* (2006.01)

(52) U.S. Cl.
CPC .... *A61M 16/0616* (2014.02); *A61M 16/0611* (2014.02); *A61M 16/0683* (2013.01); *A61M 16/0816* (2013.01); *A61M 2205/0216* (2013.01); *A61M 2205/0227* (2013.01); *A61M 2205/581* (2013.01); *A61M 2205/583* (2013.01); *A61M 2210/0618* (2013.01); *A61M 2210/0625* (2013.01)

(58) Field of Classification Search
CPC ...... A63B 23/18–185; A61M 16/0048; A61M 16/06–0655; A61M 16/0683; A61M 16/0816; A61M 16/20–201; A61M 16/208–209; A61M 2205/581; A61M 2205/583; A61M 2205/0227; A61M 13/00–006; A61F 11/00
See application file for complete search history.

(56) References Cited

U.S. PATENT DOCUMENTS

| | | | | |
|---|---|---|---|---|
| 2,887,105 A | * | 5/1959 | Brown | A61M 16/0048 D24/110.6 |
| 3,099,985 A | * | 8/1963 | Wilson | A61M 16/0048 128/203.11 |
| 3,229,689 A | * | 1/1966 | Christman | A61M 16/1075 128/203.11 |

(Continued)

*Primary Examiner* — Rachel T Sippel

(57) ABSTRACT

A device combining a treatment of ear and sinus conditions along with speech therapy and administration of medication is disclosed. The device comprises a patient facemask, adapted to cover mouth and nose of a patient, and a visual and/or audio feedback mechanism connected to the facemask and adapted to provide feedback through internal air pressure in a device's compartment. The device's compartment is adapted to be in fluid communication with the patient mouth and nose during its operation. The device may comprise a supervisor facemask. Expiration into the facemask(s) increases air pressure. An increase in air pressure within the device activates the feedback mechanism and will lead to effective middle ear and sinus ventilation. The feedback mechanism may also be used in speech therapy for feedback to the patient. Drugs may be administered into the system for treatment of airway disease of for the purpose or general anaesthesia.

15 Claims, 4 Drawing Sheets

(56) References Cited

U.S. PATENT DOCUMENTS

| | | | |
|---|---|---|---|
| 5,950,631 A * | 9/1999 | Donaldson | A61F 11/00 604/28 |
| 6,578,571 B1 * | 6/2003 | Watt | A61M 15/0016 128/200.14 |
| 2013/0211441 A1 * | 8/2013 | Bidarian Moniri | A61M 16/0605 606/192 |

* cited by examiner

DEVICE FOR SPEECH THERAPY, ADMINISTRATION OF INHALATION MEDICATION AND FOR TREATMENT OF OTITIS, SINUSITIS AND BAROTRAUMA

FIELD OF THE INVENTION

The present invention relates to a device for speech therapy, administration of oxygen and/or inhalation medication for children and also for non-surgical treatment of otitis, sinusitis and barotrauma in children and adults. More specifically the invention relates to a device for ventilation of the middle ear and the paranasal sinuses, with restoration of normal anatomy and physiology with or without the active collaboration from the patient. The device is suitable for treatment of children and adults with otitis and sinusitis and for air travellers and divers experiencing ear and/or sinus pain as a result of barotrauma. Furthermore the device allows for visual and audible feedback on respiratory techniques for effective speech therapy and may be used for administration of inhalation medication and anaesthetic induction and treatment.

FRAMEWORK OF THE INVENTION

Many children undergo speech therapy to improve their language skills, pronunciation, position of the tongue and respiratory techniques through nose and/or mouth. The present methods used until today provide only for a limited comprehension and hence collaboration especially in children and infants. A visual feedback is usually essential to confirm the correct performance of the tasks provided by the speech therapist. Current techniques for speech therapy in children are old fashioned and beside the use of a normal mirror just a few other tools are available. The present invention allows for the speech therapist to have face-to-face contact with a child using the new invention that functions as a funny game for two individuals or more. There is a visual feedback in an amusing toy for the child, where the therapist participates actively and can stimulate the child to perform the exercises related to respiration and pronunciation in a more efficient manner.

In situation where medication or oxygen is given directly in the airways a facemask may be used to cover at least the mouth and nose of the patient. This is normally the case for medication of children with airway disease such as bronchitis and asthma and may also occur at the induction of general anaesthesia in the operating theatres at hospitals. Until today the induction of general anaesthesia is considered a traumatic experience for the child, forcing a mask to be placed hermetically to avoid airway leakage on the terrified child. Currently, in order to achieve efficient ventilation medication in children with asthma and bronchitis a mouth or nose mask with a non-elastic compartment, called air chamber, is forced upon the child. Providing spray inhalation at one end the child inhales at the other end in order to provide inhalation medication into the lower airways of the child. This treatment that may be needed to perform on daily bases on children with lower airway disease such as asthma and chronic bronchitis may be rather traumatic for the child patient and the caregivers. Furthermore most part of the medication is normally accumulated in the non-elastic air reservoir and just a small fraction gets into the lower airways for treatment of the disease that is located in the bronchus or the lungs of the child patient. The present invention is aimed to provide a visual feedback and correct instruction by the parent/supervisor/physician to create a safe and reinsuring environment for the child. With the present invention the child is instructed by observing an adult to cover the nose and mouth with a similar facemask. The fact of incorporating a visual and/or audio feedback mechanism provides the possibility to assure that the child is actually breathing into the system and that accumulation of the inhalation medication takes place. The visual and/or audio feedback mechanism may consist of an elastic reservoir allowing for accumulation and gradual release of the inhalation medication and inspiration. The transportation of the inhalation medication is only to the child's airways by unilateral check valves. The adult is by this means unaffected of the inhalation medication. Furthermore turnover and the effect of the medication is higher thanks to the elastic reservoir.

Otitis is acknowledged as the most common childhood disease. Otitis is associated with extraordinary socio-economic cost for any modern society. The poor ventilation of the middle ear has been recognised as the most important factor in the high prevalence of otitis in children. Acute otitis media (AOM) is a condition characterized by the invasion of the middle ear by bacteria and/or virus causing an infection with the accumulation of pus in the middle ear accompanied by high fever and pain. This condition is the most common cause of emergent hospital visit during the childhood. Secretory otitis media (SOM) Is the accumulation of liquid within the middle ear without the symptoms and signs of an acute infection. SOM is the most common cause of childhood hearing disability.

The most common and efficient method for treatment of childhood otitis is surgical insertion of a ventilating tube (grommet) in the tympanic membrane. The surgical procedure is typically performed under general anaesthesia and is the most common surgical procedure done on children. Thousands of children are submitted to this surgery every day worldwide. Approximately one of five is expected to have recurrence of disease and may need new surgeries typically after every common cold. Approximately 10% of the children are expected to suffer from complications caused by the installation of the grommets, such as ear discharge, scars and/or permanent perforation of the tympanic membrane (5%) and growth of an epithelial tumour in the middle ear (1%), i.e. cholesteatoma. The latter is considered an incurable disease of the middle ear normally requiring several surgical interventions and continuous medical care for the rest of life. The risks associated with general anaesthesia include allergic reactions, respiratory and circulatory failure and death.

Given the high cost and the potential risks involved with grommets insertion, this surgical intervention is only recommended in children suffering from a chronic otitis with disease duration >3-6 months. This international recommendation leaves >90% of the children suffering from otitis with no active treatment, hence causing significant reduction in the quality of life of the children and their parents due to repetitive infections and/or hearing loss.

Sinusitis is caused by the poor ventilation of the paranasal sinuses, causing accumulation of liquid along with chronic or acute inflammation with or without an acute infection. Acute sinusitis is characterized by fever, pain and accumulation of pus after an infection in the paranasal sinuses. Chronic sinusitis is defined as chronic poor ventilation of the generally with inflammation of the mucosa of the paranasal sinuses with accumulation of liquid with of without polyposis. The most common therapies for sinusitis include nasal decongestants, corticosteroids, antibiotics along with surgery for to improve the communication between the nose and the paranasal sinuses to improve the ventilation. Sinusitis is a recurrent disease with no acknowledged cure, sometimes in need of repetitive surgery.

Many air travellers suffer from an acute ear and sinus pain due to insufficient middle ear and sinus ventilation to equilibrate the alteration in the atmospheric pressure. These pressure changes may damage the ear and the paranasal sinuses i.e. barotrauma. In a normal individual these cavities (middle ear and the sinuses) are filled air and are in contact with the atmospheric air via the nose. Typically in airplanes at landing the increase in the atmospheric pressure causes a tremendous force on the tympanic membranes, and the mucosa of the middle ear and the sinuses pushing those inwards (squeeze). Some adults and many children have reduced ventilation capacity in the ears and the paranasal sinuses. The sudden change in atmospheric pressure and the insufficient ventilation gives rise to an intense ear and/or facial pain with possible risk of permanent damage of the ears and/or the paranasal sinuses.

Eustachian tube is the name of the anatomical communication between the posterior part of the nose and the ears. Poor Eustachian tube ventilating function has been recognised as the most important factor for otitis. The paranasal sinuses communicate with the nose also by ductal structures and poor ventilation capacity is the fundament of sinusitis. Barotrauma of the ears and the paranasal sinuses is also believed to be caused by reduced ventilation function. Therefore, demands have been raised for a simple, non-invasive and cost effective device for middle ear and sinus ventilation.

BACKGROUND OF THE INVENTION

The history of the methods for non-invasive ventilation of the middle ear by opening of the Eustachian tube goes back to the description of Valsalva's manoeuvre by the Italian physician Antonio Maria Valsalva during the 17$^{th}$ century. This method is performed by closure of both nostrils while sealing the lips and exhaling to increase the upper airway pressure and open the Eustachian tube for middle ear ventilation. Given the complexity in the manoeuver most children and many adults are unable to perform this manoeuver. To surpass the difficulties with the Valsalva manoeuver, the Hungarian physician, Adam Politzer introduced an active pump to be connected to one nostril and while closing the other nostril and the mouth, air was actively pumped in order to increase the pressure in the upper airways and open the Eustachian tube to achieve middle ear ventilation. Even though this method was more efficient, requiring less collaboration from the patient, it was abandoned due to the pain and discomfort related to the manoeuvre. To our knowledge there are no previous non-surgical methods or devices to open the ductal communication of the paranasal sinuses.

Several devices have been developed based on these methods in order to facilitate a non-invasive opening of the Eustachian tube and middle ear ventilation, all with limited success.

Several devices for equalizing pressure in the middle ear have been demonstrated in prior art. They are based on the idea of creating a positive air pressure in the nasal/mouth cavity by having the patient to blow a balloon with the mouth or with one or both nostrils, wherein the positive air pressure of the balloon is transplanted to the nasal or mouth cavity, or are based on the Politzer technique, i.e. to force air into the nasal cavity by means of e.g. a pump.

U.S. Pat. No. 5,950,631 discloses a device for creating an increased pressure in the mouth cavity by inserting in the mouth of the patient a mouthpiece on which a balloon is mounted, and by instructing the patient to blow the balloon by expiration via the mouth while both nostrils are closed. The pressure created by the balloon is intended to be transplanted into the nasal cavity for entrance into the Eustachian tube and opening of the same. The flexibility in use is limited as the device is not adapted for nostril connection. This implies that the nostrils of the patient must be closed by hand or by the use of a nose clip. This makes the device according to this patent not user-friendly compared to the device according to the present disclosure, as it does not allow the free choice of breathing and inflating through both nostrils and/or the mouth in the same way as the present disclosure does, causing a claustrophobic sensation. Furthermore the nose dip have to be further strong to avoid air leakage and may hurt limiting the compliance. Furthermore, there is no possibility for an adult to take part in the treatment as in the present disclosure which might exclude the youngest children that probably will have difficulties in understanding the procedure. Moreover, the effect in opening the Eustachian tube is limited as the passage from the mouth cavity to Eustachian tube can be closed by closing the soft palate. Furthermore, there is no possibility for the practitioner or parent to take part in the treatment as in the present disclosure, which excludes the youngest users who cannot understand the given instructions and the device has no function in ventilation therapy nor speech therapy as described in the present invention. In conclusion, this device is limited in functionality and has a reduced compliance compared to the present disclosure.

EP0504124, U.S. Pat. Nos. 3,749,083 and 4,817,626 all have a very similar appearance and functionality. The devices are composed of a tube having one end adapted to fit one of the patient's nostrils, and the other end provided with a balloon. The devices have the nostril end of the tube adjacent to the patient's nostril and when the balloon is inflated, the pressure created by the inflated balloon is intended to be transplanted into the nasal cavity for entrance into the Eustachian tube and opening of the same. Many adults and most children experience difficulties understanding and learning how to use these devices. Even if young patients understand the instruction of usage, there are often problems related to proper positioning against the nose—if the device is too heavily pressed against the nose it actually tends to block the nostril opening, and also hurts, and if it is too loosely pressed against the nose it tends to create leakage. Many patients refuse or stop the treatment due to unpleasantness and pain and discomfort associated with the treatment. The flexibility in use is limited as the devices are not adapted for mouth connection. In clinical use many side effects have been described e.g. nasal bleeding. Furthermore to use the patient's mouth and one of the nostrils must be closed making these devices not very user-friendly compared to the device according to the present disclosure, as they do not allow the free choice of breathing and blowing through both nostrils and/or the mouth in the same way as the present disclosure does. This problem is not solved simply by providing a Y-shaped tube with two nostril openings as is proposed in EP0504124, which makes the adaptation and usage even more complicated for the young patient. The free choice of breathing is still very limited, and furthermore, having the nostrils occupied by one or two tube-end nostril plugs is not a pleasant feeling for most persons, definitely not children. Furthermore, there is no possibility for the practitioner or parent to take part in the treatment as in the present disclosure, which excludes the youngest users who cannot understand the given instructions and the device has no function in ventilation therapy nor speech therapy as described in the present invention The combination of one facemask for the child and another for the adult allows enables success in children even below the age of one year. It has been previously reported that the device according to EP0504124 has not been proven to give satisfactory results on patients younger than 5 years old, which is in contrast to the present disclosure by which it is possible to reach good results on patients even below the age of one. In conclusion these prior art devices are limited in functionality and have a reduced compliance compared to the present disclosure.

U.S. Pat. Nos. 4,749,377, 5,419,762 and 2006/0272650 disclose various types of equipment for equalizing pressure in the middle ear, all of them based on the idea of creating a positive air pressure in the nose/mouth cavity by exposing the airways to a positive air pressure created by a device delivering compressed air via an electrical air pump via a single nostril plug. The provision of a single nostril plug creates similar disadvantages as the previously mentioned devices with a balloon and a tube end for nostril connection. A difference from those previously mentioned devices, however, is that the practitioner controls the flow rate and air pressure by regulating the equipment. On the other hand, the patient has a limited control over the situation, which usually ends up in unpleasant experiences and low compliance, especially when it comes to treatment of children. These devices can be referred to as relying on the same treatment regime as the Politzer pump, which treatment is well known to be considered by younger patients to be very unpleasant, which in turn results in a poor compliance. Furthermore, there is no possibility for the practitioner or parent to take an active part to demonstrate the treatment as in the present disclosure, which excludes the youngest users who cannot understand the given instructions and the device has no function in ventilation therapy nor speech therapy as described in the present invention.

EP2629723 discloses a device for creating an increased pressure in the mouth and nose by a facemask connected to a balloon and a pump. The pressure created within the system is by inflation through mouth or nose or by pumping air into the system. This device allows for middle ear ventilation in children and infants with some limitations. The inflation of the balloon may be difficult for infants making it necessary to use the pump to force air within the system. This sudden unexpected increase of air pressure may in some cases frighten young children. A counter-pressure is created by inflating a balloon and may be increased by changing the balloon to another one with higher inflation resistance. The sudden change may in some cases be painful to the child. Furthermore, there is no possibility for the practitioner or parent to take an active part to demonstrate the treatment as in the present disclosure, which excludes the youngest users who cannot understand the given instructions and the device has no function in ventilation therapy nor speech therapy as described in the present invention. Some of the compliance issues referred to were improved by the introduction of the teddy bear to cover the pump system and causing a distraction during the treatment, however various aspects for improvement were detected and gave rise to the present invention.

U.S. Pat. No. 7,861,710 discloses a respiratory assistance apparatus and method, is based on a mechanism similar to a Continuous Positive Airway Pressure (CPAP) used for the treatment of snoring and sleep apnea, and refers to a device for Positive End Expiratory Pressure (PEEP) to treat patients suffering from lung conditions. Positive airway pressure is produced by an inlet connected to breathable pressurized gas delivered to the lungs of the patient through a breathing interface. By this method a continuous positive airway pressure in the lungs is achieved during the end expiratory phase of respiration. As continuous inlet of air in a closed mechanism would cause hazardously high pressures, an outlet in the form of an adjustable pressure valve releases the breathing gas from the system. The total amount of gas captured in the system is hence dependent of the inlet and outlet. Given that the basic construction of the device is rigid a deformable reservoir is incorporated to function as an expander especially at expiration without increasing the pressure already defined in the system by P-inlet−P-outlet. Hence, this device maintains a constant and continuous Positive Airway Pressure (=P-inlet−P-outlet), which remains during the whole faze of respiration including at End Expiratory phase in order to prevent the collapse of the alveolus in the lung tissue. The document does not refer to any regulatory effect of the deformable reservoir on the total pressure nor any effect what so ever on the upper airways. Prior art is a modification of a CPAP device to achieve Positive End Expiratory Pressure. By the means of this invention it is impossible the reach the critical opening pressure in the Eustachian tube to ventilate the middle ear. Furthermore, there is no possibility for the practitioner or parent to take an active part to demonstrate the treatment as in the present disclosure, which excludes the youngest users who cannot understand the given instructions and the device has no function in ventilation therapy nor speech therapy as described in the present invention.

SCOPE OF THE INVENTION

A new device is therefore disclosed for creating an overpressure in the upper airways in order to open up the Eustachian tube and the sinus ducts, forcing the air into the middle ear and the sinuses to achieve effective ventilation. The device can be used both by children and adult either independently or in collaboration as a game between the adult/parent and the child. The adult may perform the treatment simultaneously and maintain a visual contact with the child and to create a harmonic and secure environment for the child.

The device comprises a patient interface adapted to cover at least the mouth and nose of the patient and a visual and/or audio feedback mechanism, which is connected to the patient interface and adapted to provide feedback to the patient on an internal air pressure in a compartment of the device. This compartment is adapted to be in fluid communication with the patient mouth and nose, during operation of the device.

According to one embodiment, the device comprises a body having an inner surface defining the compartment with a first opening in communication with the compartment, wherein the patient interface is connected to the first opening, and a second opening in communication with the compartment, wherein the visual and/or audio feedback mechanism is connected to the second opening. The second opening may be perpendicular to the first in one embodiment but other geometrical relations are also envisaged.

According to a further embodiment, the device comprises a supervisor interface adapted to cover at least mouth and/or nose of a supervisor and wherein the compartment is adapted to be in fluid communication with the supervisor mouth and nose, during operation of the device.

According to a further embodiment, the body is elongated and wherein the first opening and a third opening for connection to the supervisor interface are arranged at a distance from each other in the longitudinal direction of the body. The elongated body may be in the shape of a tube or similar structure, preferably with a main extension along a straight line, wherein the compartment may form a passageway extending in parallel with the straight line. The passageway may form a through-going hole. Other geometrical configurations of the tube are also envisaged.

In one embodiment of the device the interface is a facemask covering at least the nose and mouth of the patient and a supervisor.

In another embodiment of the device and air inlet is provided on the horizontal tube for introduction on inhalation medication. Furthermore check valves allow for the transportation of the medication uniquely in the direction of the child. Hence the adult will not be affected by the medication.

Thus, two interfaces/facemasks, one for the adult supervisor and one for the child patient, are adapted at the openings on the tube in order to cover at least nose and mouth of the child and at least nose and/or mouth of the adult or supervisor. Further, two check valves may be incorporated into the facemasks. Further, a filter and a check valve may be provided within the tube on each side. Further, an adjustable or non-adjustable pressure control valve, a sound valve and/or an air pressure sensitive mechanism for visual feedback and a safety valves for outlet of air may be provided.

Furthermore the visual and/or audio feedback mechanism may accumulate inhalation medication provided and release the medication gradually at inspiration into the airways of the patient.

The facemasks are preferably adapted to cover at least the nose and mouth of the patient and supervisor, respectively. Straps may be provided to facilitate the hermetic positioning of the facemasks. According to one example operation, at inspiration the air enters the lungs of the subjects by the check valves in the facemasks on each side. At expiration the air passes the facemasks and enters into the tubular structure. Thanks to the check valves the air can only be transplanted in the direction of the second perpendicular opening, passing by the adjustable pressure valve and into the air pressure feedback mechanism. This manoeuver can be repeated by any expiratory effort. The adult supervisor will start to instruct the child/patient in the usage, and the child follows with an efficient visual and audible feedback on the correct performance of the manoeuvres by mouth and/or nose. In speech therapy pronunciation of difficult vowels and consonants can be trained. For the treatment of ear and sinus conditions resistance can be produced by the adjustable valve in the perpendicular second opening. Increasing resistance in the system will increase the pressure produced in the upper airways of the subject. In fact any expiration of air in laughing, coughing, sneezing, screaming and even crying of pain (which may be the case of children experiencing ear ventilation difficulties in airplanes) created by nose and/or mouth will automatically be captured within the system thanks to the one-way security valves, creating a positive pressure within the device that will be transplanted to the upper airways of the user(s), leading to the opening of the Eustachian tube and or the ducts of the paranasal sinuses causing successful ventilation. The interface/facemask provided for the adult allows for direct eye contact and demonstration to the child of correct usage and will create safe, harmonic and efficient conditions for therapy. Furthermore the adult may use the device for self-treatment in case of ear or sinus related problems. The device can be used of one or two persons either individually or simultaneously. In the latter case, visual eye contact will enhance the comfort and confidence of the child to take part of the game with the adult.

The tube may be provided with an adjustable pressure control valve to alter the resistance created by the system hence controlling the effort created by the child/adult to inflate into the system. A sound valve may be provided after the adjustable pressure control valve and is activated when the desired pressure is reached in order to give audible feedback to the adult and the child. In the case of speech therapy the sound valve may be absent in order to focus on the pronunciation of the child and allow for correction and instructions accordingly. An air pressure sensitive mechanism may be incorporated after the sound-creating valve. This mechanism is activated by inflation when a certain pressure level is reached. The mechanism incorporated is put in motion to give visual feedback to the adult and the child. The pressure sensitive mechanism is typically in the form of a party blowout but other embodiments are also envisaged e.g. elastic inflatable balloon, tube filled with water or other liquids, digital sound and visual feedback. This mechanism may be hermetic or may allow for outlet of air controlled by an adjustable security valve. The presentation of the visual and/or audio feedback mechanism may be as a balloon, a party blowout or a transparent water-filled chamber allowing for the entrance of visible air bubbles whenever activated. In the latter case the visual and/or audio feedback mechanism may provide as elastic reservoir for accumulation of medication for gradual release at inspiration. A pressure relief valve and/or an apparatus for pressure monitoring may be provided in the horizontal tube for the control of the total pressure created within the system with the security valve being activated to avoid hazardously high pressures in the system.

With the interface/facemask adapted hermetically with the straps, the air will enter by the check valves provided in the masks at inspiration. Air pressure is created by expiration into the facemask via mouth and/or nose, either by the adult, the child or both and is captured within the system by the one-ways security valves. The amount of air that enters the device primarily controlled by the adjustable pressure control valve which may be set at zero (at speech therapy) or higher levels dependent on the condition to be treated. A high resistance will give rise to an increase in the airway pressure to finally reach the critical opening pressure of the Eustachian tube and the ducts of the paranasal ducts to achieve successful ventilation. The sound valve and the pressure sensitive mechanism are activated to allow for feedback to the users and the supervisor of correct manoeuvre.

In one embodiment, filters are provided on each side of the horizontal tube, preventing the entrance of microorganisms and germs within the tubular structure in order to avoid contagious diseases. The sound valve may create an audible feedback to the child and the adult for the confirmation of the correct performance of the manoeuver. The air sensitive mechanism will provide a visual feedback to the adult and the child of the correct performance of the manoeuvre.

In another embodiment of the present invention exterior air inlet is only provided on the adult facemask. Hence the child inhaled only the air within the system.

The visual and/or audio feedback mechanism may also allow for accumulation of inhalation medication with gradual release at inspiration, especially with the latter is an elastic air reservoir. Thanks to check valves the air inspired by the adult is provided from the exterior whilst the air inspired by the child is provided from the closed system with the possible ventilation medication that will uniquely affect the child.

Advantages of the Invention

According to at least one embodiment of the present invention, the efficacy of treatment is dependent on covering at least the nose and mouth hermetically by the facemask. To overcome the difficulties presented by the prior art, the present invention allows for the increase of the pressure within the system by the adult supervisor performing the exact same manoeuver face to face with the child with continuous eye contact. This embodiment will allow for direct eye contact for adult supervisor to correctly instruct the child patient with audio-visual feedback on the manoeuvre. The supervisor may blow into the system and create an overpressure. An elastic strap may be provided on each facemask to hold the facemask in position without the need of any assistance. By this the adult is able to encourage the child by doing the exact same manoeuvre, underlining the safety aspects, giving practical instructions of use and creating a comfortable and trustable environment for the child to adhere to the treatment. The filter provided for capture of germs will not allow for passage of any contagious particles from the adult supervisor to the child patient. Other embodiments of the present invention may be used at speech therapy with the adjustable valve set on 0, i.e. little resistance created within the system with only visual and audible feedback. It is also possible to increase the resistance gradually by the adjustable valve to create the contrapressure necessary to open and ventilate the middle ear and the paranasal sinuses, hence sudden increase in pressure is prevented. Furthermore, the present device is small and practical, allowing for an efficient and treatment both at home, at hospitals/clinics and on airplanes, trains, submarines and cars or at hyperbaric oxygen therapy chambers. In an alternative embodiment of the present device it is possible to give oxygen or medical ventilation medication in the device for treatment of respiratory diseases and also anaesthetic induction in the operating theatres. In this embodiment the visual and/or audio feedback mechanism functions as an accumulator and releaser of the medication into the airways of the child. Furthermore a unidirectional check valve allow for the transportation of the medical into the airways of the child or patient exclusively.

The present disclosure is superior in effect primarily due to significantly higher compliance compared to the technical solutions of the prior art, and this is for several reasons.

In any treatment the first and most important rule is to actually accept the treatment. In the case of children many challenges are expected given the limited comprehension and collaboration. Using the present device, the child is more confident watching and following the adult in all the steps of the treatment. Speech therapy can be performed in a much more efficient manner with audio-visual feedback directly to the child and the therapist.

In treatment of otitis and sinusitis the patient does not have to need to perform complicated manoeuvres such as breathing out and simultaneously swallow to get the desired effect. Any expiratory effort will lead to efficient ventilation. Most of the prior art devices are restricted to either mouth or nose application, or even to one single nostril, having the other nostril closed by e.g. a finger. The flexibility of usage, teamwork, adaptation to the particular patient and the trustable harmonic environment are the key words of the great success in therapy with the present invention. The methods and equipment used for speech therapy and drug administration in the airways still follow the traditional devices available not taking into account the point of view and the insecurity that many times are present in children and infants. Administration of ventilation therapy is facilitated by the proactive and instructive character of the device. The amount of ventilation drug that reached the lower airways (larynx, lungs and bronchus) is significantly higher thanks to the elastic reservoir/releaser. None of the prior art presented here are adaptable for speech therapy, drug administration of treatment of chronic sinusitis.

Thus it is an object to provide an improved device for speech therapy, administration of medication in the airways and ventilation of the middle ear and paranasal sinuses of adults and children, suffering from otitis, sinusitis, for air travellers, high mountain enthusiasts, personal at the submarines and patients in hyperbaric oxygen therapy with difficulties in air pressure equilibration between the middle ear and the sinuses.

SUMMARY OF THE INVENTION

The invention herein regards a device for efficient speech therapy at clinics, drug administration and anaesthetic induction at hospitals and/or for adequate ventilation of the middle ear and the paranasal sinuses for home treatment and on airplanes, submarines, hyperbaric oxygen chambers, trains and cars.

The object is achieved via a device according to claim 1. Thus, it is achieved by a device for therapy and/or treatment of a patient, wherein the device comprises a patient interface adapted to cover at least both mouth and nose of the patient and a visual and/or audio feedback mechanism, which is connected to the patient interface and adapted to provide feedback to the patient on an internal air pressure in a compartment of the device, which compartment is adapted to be in fluid communication with the patient mouth and nose, during operation of the device.

More specifically, the device is adapted for creating an increased air pressure in the compartment by expiration into the compartment. For example, the patient may blow into the interface by means of the diaphragmatic pressure, wherein the air pressure in the compartment is increased and transplanted through the Eustachian tube for middle ear ventilation.

The patient interface is preferably adapted to fit tightly against the face of the patient around the mouth and nose so that an air chamber may be formed between the face and an inner surface of the interface. More specifically, the patient interface is preferably adapted to engage hermetically with the face of the patient around the mouth and nose. Elastic straps facilitate the hermetic adaptation of the facemasks.

Further, the compartment may be arranged to be in fluid communication with the patient mouth and nose via a valve. The compartment may partly be formed by the air chamber between the face and an inner surface of the interface. Further, the visual and/or audio feedback mechanism may be connected directly to the interface or connected to the interface via a connecting structure. Further, the compartment may partly be formed by such a connecting structure between the interface and the visual and/or audio feedback mechanism.

According to one embodiment, the visual and/or audio feedback mechanism is adapted to be in fluid communication with the patient interface via the compartment.

According to a further embodiment, the device comprises a body having an inner surface defining the compartment with a first opening in communication with the compartment, wherein the patient interface is connected to the first opening, and a second opening in communication with the compartment, wherein the visual and/or audio feedback mechanism is connected to the second opening.

According to a further embodiment, the device comprises an air flow resistance means for providing a counter pressure in the compartment during operation of the device.

The airflow resistance means may be integrated in the visual and/or audio feedback mechanism, which may be the case when the visual and/or audio feedback mechanism is hermetic, such as in the case of a balloon. According to an alternative, the airflow resistance means is separate from the visual and/or audio feedback mechanism. More specifically, the airflow resistance means may be formed by a restriction or valve, which may be adjustable.

According to a further embodiment, the airflow resistance means is arranged at the second opening.

According to a further embodiment the airflow means is a reservoir for accumulation and gradual release of medication in case or drug administration for ventilation therapy.

According to a further embodiment, the device comprises a supervisor interface adapted to cover at least mouth and/or a nose of a supervisor and wherein the compartment is adapted to be in fluid communication with the supervisor mouth and nose, during operation of the device.

According to one example, the visual and/or audio feedback mechanism is in fluid communication with the supervisor interface via the compartment.

Further, this embodiment creates conditions for a visual feedback of not only the feedback mechanism but also any manoeuver/action of the supervisor positioned in a face-to-face relationship with the patient.

According to one example, the patient and/or supervisor interface may be transparent for visual feedback and encouraging the child patient to mimic/repeat the manoeuver/action of the adult supervisor or therapist.

According to a further embodiment, the supervisor interface is arranged in a mirrored relationship relative to the patient interface.

According to a further embodiment, the body has a third opening in communication with the compartment.

According to a further embodiment, the supervisor interface is connected to the third opening.

According to a further embodiment, the body is elongated and wherein the first opening and the third opening are arranged at a distance from each other in the longitudinal direction of the body.

The elongated body may be in the shape of a tube or similar structure, preferably with a main extension along a straight line, wherein the compartment may form a passageway extending in parallel with the straight line. The passageway may form a thoroughgoing hole.

According to a further embodiment, the first opening and the third opening are arranged at opposite ends of the body in the longitudinal direction of the body.

According to a further embodiment, the second opening is positioned between the first opening and the third opening in the longitudinal direction of the body.

According to a further embodiment, the device comprises a one-way valve positioned between the patient interface and the visual and/or audio feedback mechanism for allowing air passage only in a direction from the patient interface towards the visual and/or audio feedback mechanism.

According to a further embodiment, the device comprises a one-way valve positioned between the supervisor interface and the visual and/or audio feedback mechanism for allowing air passage only in a direction from the supervisor interface towards the visual and/or audio feedback mechanism.

According to a further embodiment, the device comprises a one-way valve associated to the patient interface for communication with ambient air for allowing air passage only in a direction to the patient interface.

According to a further embodiment, the device comprises a one-way valve associated to the supervisor interface for communication with ambient air for allowing air passage only in a direction to the supervisor interface.

According to a further embodiment, the device comprises a security valve in communication with the compartment for releasing air from the compartment if the internal pressure reaches a predefined threshold.

According to a further embodiment, the device comprises a further opening in communication with the compartment for entering medication, drugs and/or oxygen to the compartment.

According to a further embodiment, the visual and/or audio feedback mechanism comprises an expandable chamber.

According to a further embodiment, the visual and/or audio feedback mechanism comprises a party blowout.

According to a further embodiment, the visual and/or audio feedback mechanism comprises a liquid-filled chamber.

According to a further embodiment, the expandable chamber functions as an elastic reservoir for accumulation and release of ventilation drugs.

According to one example, the interface comprises a cup-shaped portion, wherein a first end portion has a curvature corresponding to the shape of the face of the user. Further, the interface has a tapering shape from the first end portion towards a second end portion, which is provided with an opening forming an air passage. Further, the interface may be adapted to cover the mouth and nose of the user, while leaving the eyes of the user outside of the interface.

According to a further embodiment, the patient interface comprises a facemask.

According to a further embodiment, the supervisor interface comprises a facemask.

According to a further embodiment, the interface is held in position by straps.

It may be noted that the contents of claims may be combined in many different ways not limited to the specific combinations resulting from the specific claim dependencies.

According to an example operation, at inspiration the air enters without resistance and at expiration the visual and/or audio feedback mechanism is put in action. An adjustable valve may be arranged to alter the resistance within the system. A sufficient increase of air pressure in the device is transplanted via the nose and mouth to open the Eustachian tube or the ducts of the paranasal sinuses and forcing the air into the middle ear and the sinuses for effective ventilation.

Other objects and advantages of the present invention will become obvious to the reader and it is intended that these objects and advantages will be within the scope of the present invention.

DETAILED DESCRIPTION OF THE INVENTION

Preferred Embodiments

The device disclosed in the present document comprises components connected to a tube or similar structure composed of one or several interconnected tube shaped components, and hereafter referred to as the connecting tube.

Figure 1:
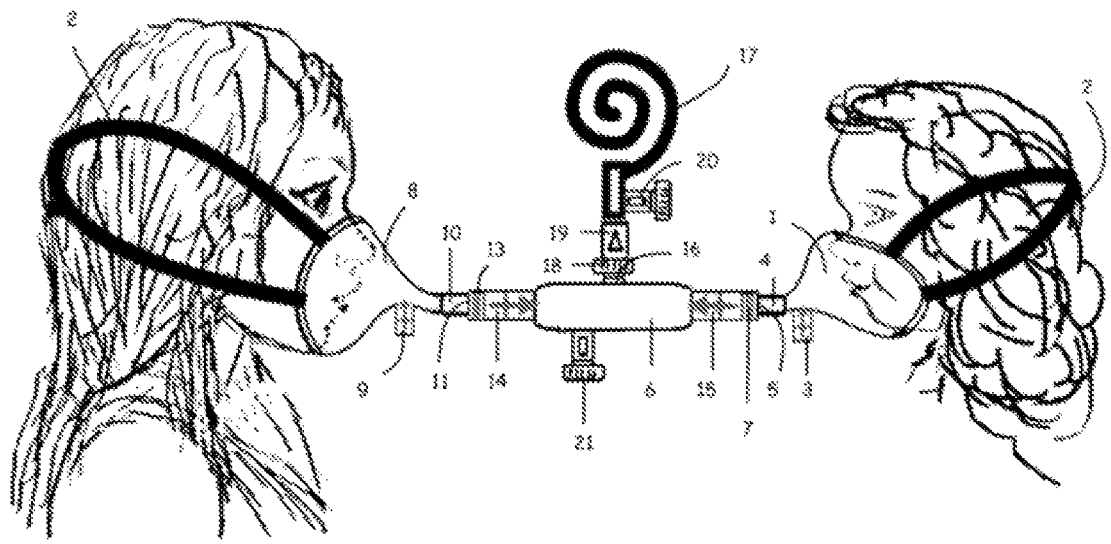
FIG. 1 is a perspective view showing a representative embodiment of the present invention mounted over the nose and mouth of the users with the air pressure sensitive mechanism being a party blowout.
Figure 2:
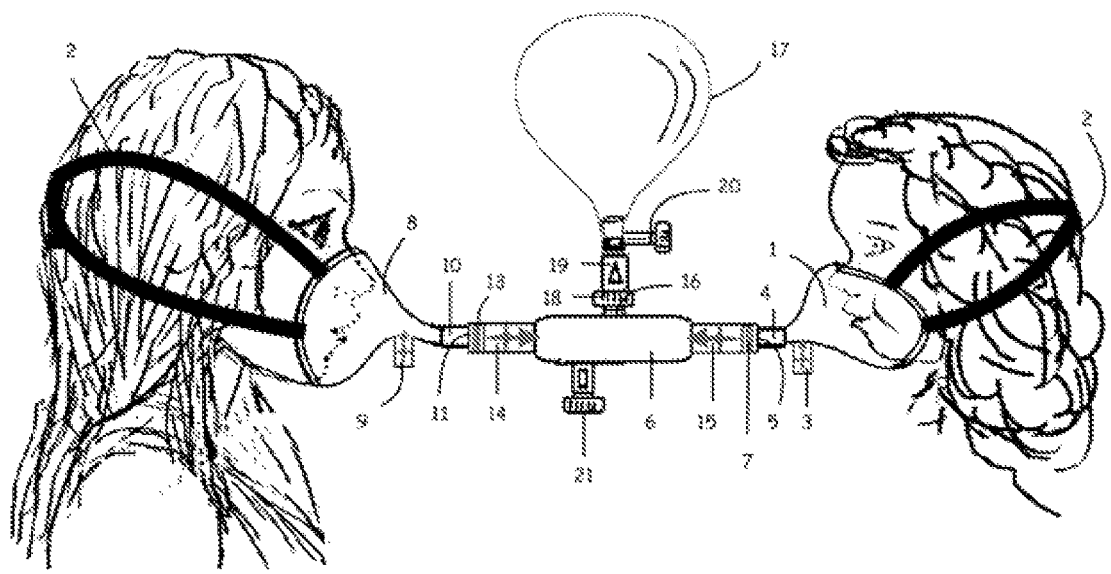
FIG. 2 is a perspective view showing an alternative embodiment of the present invention mounted over the nose and mouth of the users with the air pressure sensitive mechanism being a balloon.

Referring to FIGS. 1 and 2, a patient facemask (1) is provided as a face interface, adapted by the strap (2) to provide a tight-fitting cover for at least both nose and mouth of the patient. The patient facemask (1) is provided with a first check valve (3) allowing for air entrance at inspiration and an opening (4) for connection to the first horizontal opening (5) of the connecting tube (6), wherein the opening (4) of the patient facemask (1) communicates with the mouth/nose-interface creating an open air channel through the patient facemask (1). The patient facemask (1) is preferably removable from the first horizontal opening (5) of the connecting tube (6) in order to allow a patient facemask (1) of a size well suited for the patient in question to be provided, e.g. Infants, children and adults. Any size of the patient facemask (1) is envisaged in this context. The patient facemask (1) can be disposable or not, and can be provided with a first filter (7) for cleaning the breathing air before entering the device. The patient facemask (1) does not have to be a conventional facemask, but could be any kind of structure that can provide an essentially tight-fitting cover over the nose and mouth of a patient, and that is able to conduct air between the mouth/nasal cavities and the other parts of the device. The part of the patient facemask (1) coming into contact with the patient's skin can be made of silicone, gel, leather, rubber, plastic, e.g. as an air-filled, gel-filled or water-filled pillow, or can be made of any material that fits the facial contours in a sealing manner and is acceptable in terms of human health. The rest of the patient facemask (1) can be made of similar material, however typically a more rigid structure. The facemask may be foldable to save space. Elastic or non-elastic strap(s) (2) are provided to ensure tight-sealing mask on the face with a minimum or no leakage or air for correct performance of the manoeuvre. Several geometrical configurations of the strap (2) are envisages including but not limited to single line, X, V, Y-shaped straps. The first filter (7) provides a barrier for entrance of germs and contagious microorganism into device.

A supervisor facemask (8) is provided for the supervisor, face interface, adapted to provide a tight-fitting cover for at least both nose and/or mouth of the supervisor. The supervisor facemask (8) is provided with a second one-way valve (9) for air entrance at inspiration and an opening (10) for connection and air passage at expiration to the second horizontal opening (11) of the connecting tube (6). The material and the size of the supervisor facemask (8) follow the same guidelines of the opposite one provided for the patient facemask (1). A strap (2) and a second filter (13) are also incorporated as for the opposite side. Check valves (14) (15) are provided allowing for unilateral air passage in the direction of the arrows. The third check valve (14) allows only for air passage from the second horizontal opening (11) in the direction of the connecting tube (6) and the perpendicular opening (16). The fourth check valve (15) allows for a unilateral air passage from the first horizontal opening (5) in the direction of the connecting tube (6) and the perpendicular opening (16). A second pressure relief valve (21) is also provided to allow monitoring the pressure, and avoiding the creation of a pressure that may cause injuries to the patient. This second pressure relief valve (21) may adjustable or fixed set to pressures between 0-120 cm $H_2O$.

A visual and/or audio feedback mechanism (17) is provided on the perpendicular opening (16) of the connecting tube (6). Preferably, the visual and/or audio feedback mechanism (17) is a party blowout, but it could also be a balloon, water-filled chamber to provide a visual feedback to the user(s). Other technical solutions based on air reservoirs in combination with digital pressure control and pressure monitoring and feedback are also envisaged. The visual and/or audio feedback mechanism (17) is preferably removable, allowing for substitution in case of malfunction due to wear damage. The visual and/or audio feedback mechanism (17) is preferably hermetic and activated by the increase of air pressure e.g. a party blowout, balloon or a transparent liquid filled chamber where the air bubbles will function as the visual feedback for correct performance of the manoeuvre. The visual feedback and/or audio mechanism (17) may also function as an elastic reservoir for accumulation ventilation drugs with gradual release at inspiration. Between the visual and/or audio feedback mechanism (17) and the perpendicular opening (16) of the connecting tube (6), an adjustable pressure valve (18) is provided. The adjustable pressure valve (18) can be set to open at 0-100 cm $H_2O$. Within the visual and/or audio feedback mechanism (17) a sound valve (19) is incorporated typically creating the sound of a party blowout. An adjustable first pressure relief valve (20) may also be provided to allow for the release of air from the system. The first pressure relief valve (20) may be set to 0-120 cm $H_2O$.

At inspiration air enters through the one-way valves (3) (9) to the patient and the supervisor respectively. Air pressure can be created by the patient by breathing or blowing into the patient facemask (1) via mouth and/or nose, and/or can be created by the supervisor, normally an adult in consecutive steps or simultaneously. The air pressure created propagates along the inside of the connecting tube (6) to the different components, activating the visual and/or audio feedback mechanism/reservoir (17). When the supervisor demonstrates the idea of the treatment with an amusing audio-visual feedback to the patient, the latter is encouraged to repeat the same manoeuver. By blowing into the patient facemask (1) the patient will force the air into the connecting tube (6) and given the third check valve (14) the air will only be forced to the perpendicular opening (16) and will find its way through the adjustable pressure valve (18) to reach the sound valve (19) and the visual and/or audio feedback mechanism (17) as previously described. The increased pressure in the mouth and nose cavity will propagate to open the Eustachian tube and the sinus ducts forcing the air in the middle ear and the sinuses for efficient ventilation of both. The air is then successively expulsed by the first pressure relief valve (20), which may be set at 0-120 cm $H_2O$. For use during speech therapy the resistance in the adjustable pressure valve (18) and the first pressure relief valve (20) are set at a minimum to reduce the contra pressure created within the system. The sound valve (19) may also be removed.

Figure 3A:
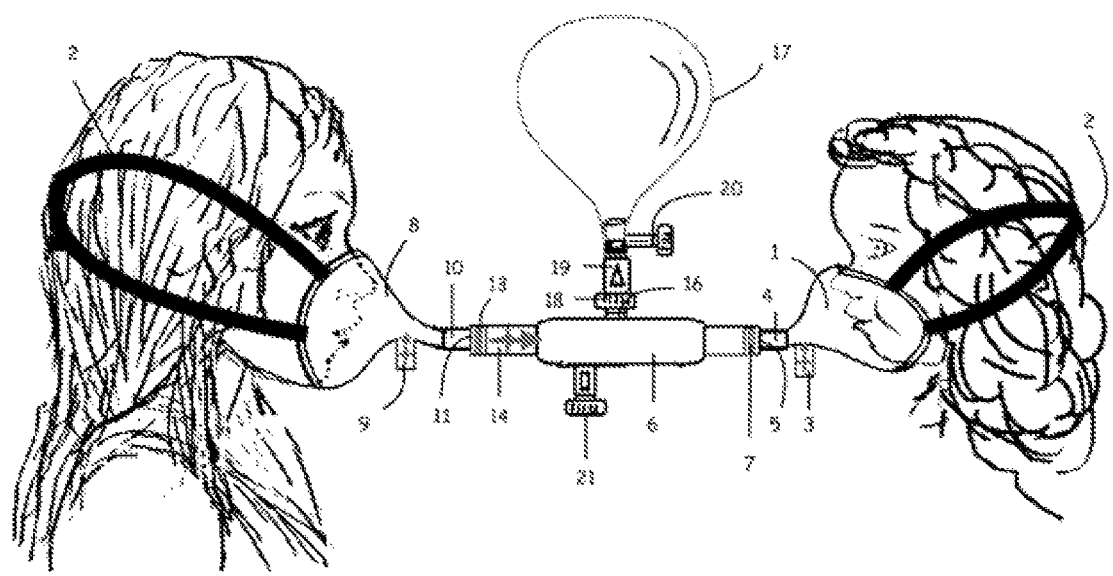
FIG. 3a discloses an alternative embodiment of the device relative to FIG. 2 with the removal of the fourth check valve (15) allowing for the air with or without drugs to propagate freely in the direction of the child patient for treatment of sinus and ear related conditions with air pressure and treatment of lower airway disease by ventilation medication.

Referring to FIG. 3a, in an alternative embodiment, the fourth check valve (15) Is removed. At inspiration by the patient the air enters through the first check valve (3) and/or through the second horizontal opening (11) of the connecting tube (6) at expiration by the adult. When the child exhales, the air from the patient facemask (1) will only go in the direction of the perpendicular opening (16) as previously described. The resistance created at expiration is dependent of the adjustable pressure valve (18) and the counter pressure in air visual and/or audio feedback mechanism/reservoir (17). Hence the air blown into the patient facemask (1) by the patient stays within the system and the air blown through the supervisor facemask (8) will propagate into the connecting tube (6) and will be trapped within the system increasing the pressure within the system. In this way the adult will also help in creating a positive pressure if the child is unable to do so by itself.

Figure 3B:
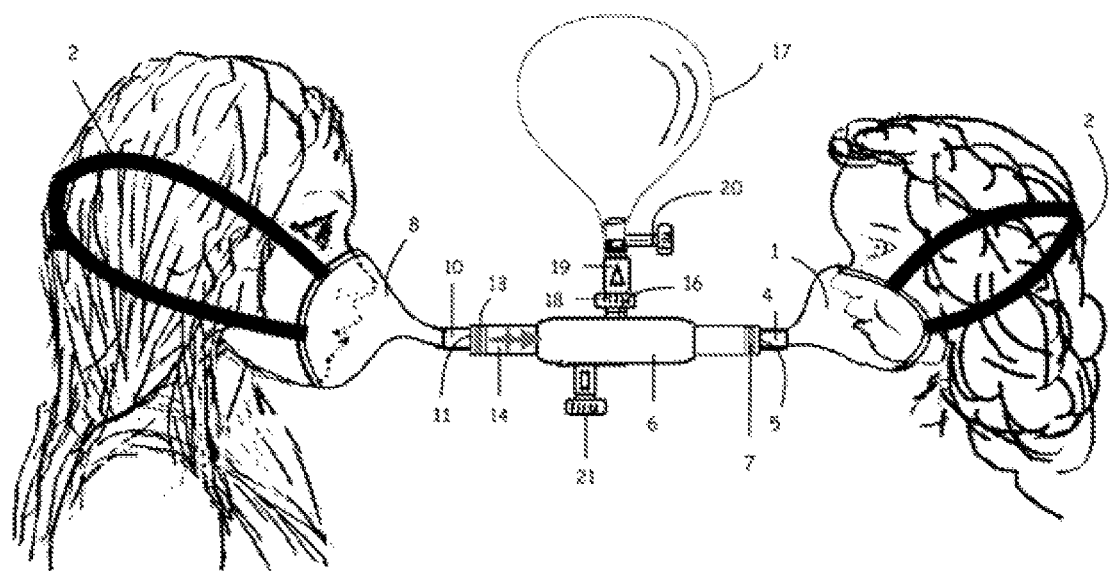
FIG. 3b discloses a further alternative embodiment of the device relative to FIG. 3a with the removal of the one-way valves (3) (9) of the facemasks (1) (8).

The check valve (3) may be removed allowing for air entrance only through the one-way valve (9). In FIG. 3b, there is a simplified version of 3a, where both one-way valves (3) (9) are removed. In this embodiment the only entrance of air is by the supervisor facemask (8) from the supervisor's lungs at expiration. Given the superior lung capacity in the adult there will always be a surplus of air pressure with a gradient from the adult to the child.

Figure 4:
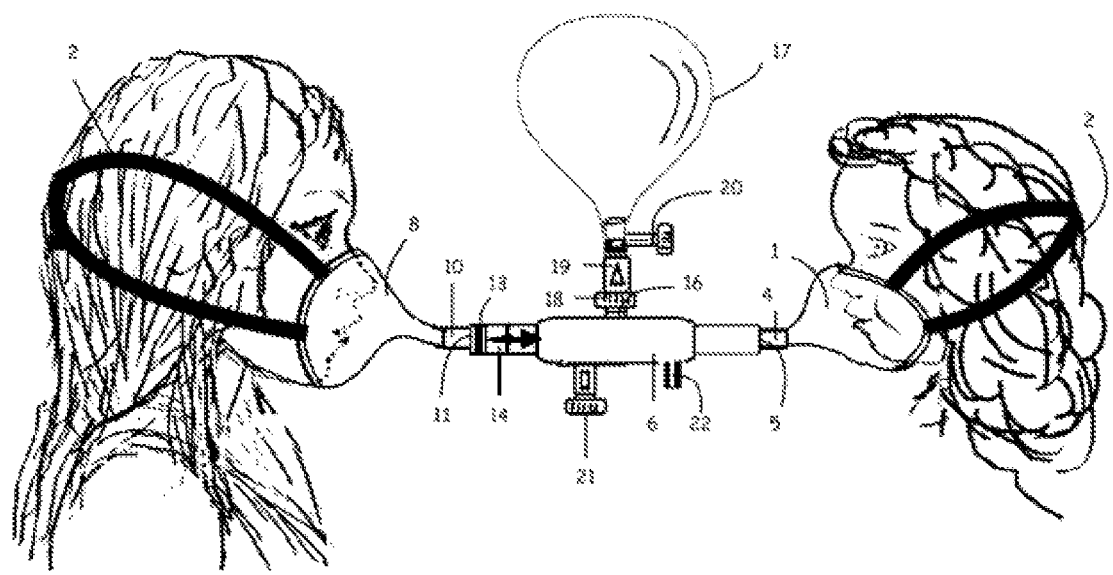
FIG. 4 is an alternative embodiment of the device for use for drug and oxygen administration in additional opening (22) at home or at hospital typically for treatment of lower airways disease such as asthma, bronchitis and for anaesthetic induction at the operating theatre.

In FIG. 4, the same embodiment as in FIG. 3b is provided with an additional opening (22) and the removal of the first filter (7) at the connecting tube (6) for the entrance of medication for ventilation therapy in airway disease such as asthma and bronchitis and also for anaesthetic induction and oxygen therapy. In this embodiment the adjustable pressure valve (18) is set at 0 cm $H_2O$ for free air passage in both directions, the second pressure relief valve (21) is set at a high level, for instance 120 cm $H_2O$, in order to avoid any leakage and the visual and/or audio feedback mechanism (17) Is an elastic component such as a balloon. In this embodiment the adult supervisor, preferably a parent, may assist the child and by using the supervisor facemask (8) instructing and creating a safe environment for the child. The anesthesiologist or practitioner will introduce the medication from the additional opening (22) and the drug will stay within the connecting tube (6) and the visual and/or audio feedback mechanism (17) and will successively enter the airways of the child through the first horizontal opening (5) of the connecting tube (6) and further into the patient facemask (1). Furthermore the third check valve (14) prevent the entrance of the inhalation drug into the facemask and the airways of the supervisor. However by exhaling, the supervisor may also assist in forcing the drug towards the patients interface.

Figure 5:
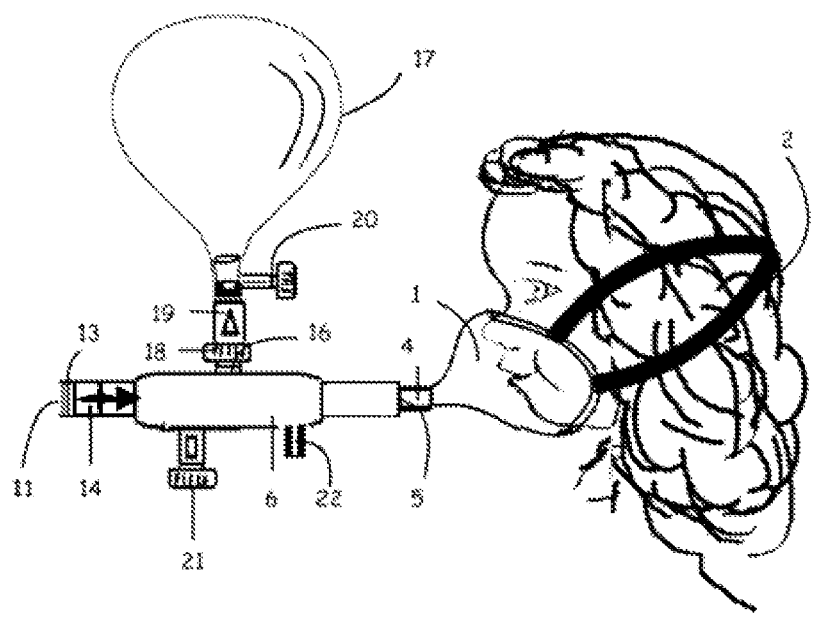
FIG. 5 is an alternative embodiment of the device according to FIG. 4 without the supervisor facemask (8).

Referring to FIG. 5, in an alternative embodiment of the device there is neither a supervisor facemask (8), nor the check valves (15) (3). The inspiratory air enters without any resistance from the second horizontal opening (11) of the connecting tube (6). At expiration the air is captured within the system by the action of the third check valve (14), forcing the air in the direction of the perpendicular opening (16) as previously described. For speech therapy the child will be allowed to visualize the face and the lips of the therapist. For this purpose the pressure at the adjustable pressure valve (18) is set to 0 cm $H_2O$. Hence no resistance is created within the system. For treatment of ear and sinus related conditions, the resistance in the adjustable pressure valve (18) is increased to the desired level and if necessary the adult may assist the child by blowing by mouth into the second horizontal opening (11) of the connecting tube (6) to assist the child to increase the pressure within the system, hence achieving efficient middle ear and/or sinus ventilation.

Figure 6:
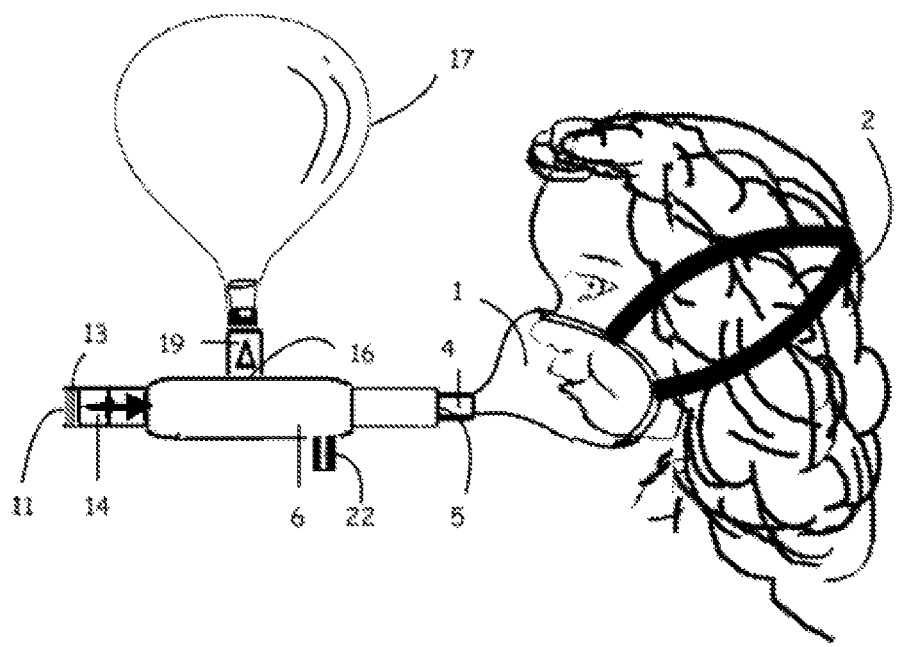
FIG. 6 is a further alternative embodiment of the device according to FIG. 5 with the removal of the second pressure relief valve (21).
Figure 7:
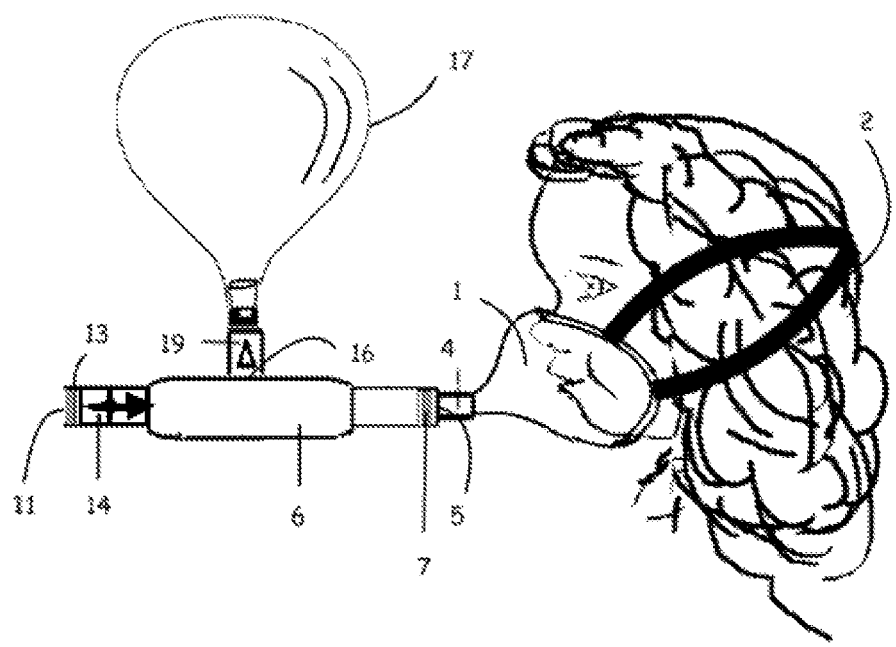
FIG. 7 is another alternative embodiment of the present invention without the additional opening (22).

In an alternative embodiment of the device, described in FIG. 6, at inspiration from the patient facemask (1) the air enters uniquely from the second horizontal opening (11) and is captured in the device by the action of the third check valve (14). With repetitive inspiration a pressure is build up within the system to create a positive atmospheric pressure, hence inflating the visual and/or audio feedback mechanism/reservoir (17), with no release of the air. The visual and/or audio feedback mechanism (17) in the figure is an expandable air reservoir such as a balloon. At administration of inhalation medication from the additional opening (22), the drug is transplanted into the system through the connecting tube (6) and the perpendicular opening (16) to the visual and/or audio feedback mechanism/reservoir (17). At each inspiration gradual release of the medication from the visual and/or audio feedback mechanism (17) takes place. Thanks to the high atmospheric pressure in the system and the gradual release from the visual and/or audio feedback mechanism/reservoir (17), the transfer of medication through the patient facemask (1) and into the lower airways including the larynx, bronchus and the lungs of the patient, is facilitated and highly efficient.

The connecting tube (6) is preferably made of plastic of sufficient rigidity to provide air-tight connections to the various components connected to it, and for easy handling of the device. The connecting tube (6) may also have details made of other materials like rubber and glass and parts of it may be more flexible to make it adjustable in length and angulation if so desired. The connecting tube (6) can be made entirely as one unit, or can be composed of several parts connected to each other, e.g. parts of tubes, joints and gaskets. Several geometrical configurations of the connecting tube (6) are envisages with the possibility of the connection of prolongation tubes to the horizontal openings (5) (11).

In an alternative embodiment of the invention more than two facemasks are connected to the connecting tube (6) by the same mechanisms involved to allow for more persons to participate in the treatment that would be performed in group. Group therapy could be provided for children suffering from chronic otitis media, in order to encourage one another in the correct performance of the treatment. Furthermore children undergoing speech therapy may also benefit from treatment of 2 or more patients at the same time along with the supervisor or therapist.

Several different options for the elastic, or non-elastic straps are envisaged. The straps (2) facilitates the positioning of the facemasks (1) (8) to create an air-sealed connection between the face and the facemask with the minimum of effort enhancing compliance and efficiency as compared to prior art.

The visual and/or audio feedback mechanism (17) may be a party blowout, an elastic reservoir such as a balloon or a chamber filled with liquid. In the case of balloon several resistance and counter pressures are envisages typically form 20 cm $H_2O$ up to 100 cm $H_2O$ for the creation of counter-pressure necessary in the treatment of ear and sinus condition. The water-filled chamber may contain liquids such as oil and water and the resistance created is dependent of the amount of liquid presented and may be adjusted dependent on the condition to be treated.

The arrangement with the one-way valves (3) (9) according to the foregoing description of the preferred embodiments allows the patient to breathe freely without substantial resistance when the device is tight-fittingly mounted at the mouth and nose of the patient and the supervisor. This minimizes the sensation of discomfort in wearing the device and is therefore an advantage compared to prior art devices.

The device according to the present disclosure is preferably intended for drug administration by ventilation, speech therapy and also treatment of otitis, sinusitis or in situations where sudden change of atmospheric pressure causes difficulties of ventilation and the equilibration of the pressures. Children and adults can equally be treated with success by the device of the present invention. The device is advantageously used by children as well as adults when suffering from otitis, sinusitis or when diving, flying or performing other activities that may induce disadvantageous pressure gradients in ears and the paranasal sinuses. Treatment using the device can be performed at any stage of dysfunction and any degree of symptoms related to pressure gradients. The treatment can also be prophylactic to prevent infection, surgeries and other chronic diseases of the ears and the paranasal sinuses. The device is also meant as an efficient mean of instruction of children in need of speech therapy or medication by inhalation.

The visual and/or audio feedback mechanism (17) is primarily incorporated to give a visual feedback to the user but may also help in adjusting the desired pressure. Using a balloon for this regulator purpose, it must have an elasticity which gives an inflating resistance in order to achieve a therapeutic effect, whereby a counter pressure is created.

The second pressure relief valve (21) within the connecting tube (6) can be set on a desired pressure. This second pressure relief valve (21) is opened whenever the pressure in the system exceeds a certain level, e.g. 20-120 cm $H_2O$, in order to avoid injuries or pain due to high pressures in the treatment.

In summary, the device according to the present disclosure relies on a combination inhalation therapy performed by nose or mouth to ventilate the middle ear and the paranasal sinuses. This combination has been proven to give surprisingly satisfactory therapeutic results for curing otitis and sinusitis. The unexpected results are much better than the sole additive effect of any previous therapies known before. This will be described more in detail in the following examples. Moreover, in a preferred embodiment the present disclosure relies on the psychological dimension of treatment of children by providing audio-visual feedback compliance, enhanced trust and security by the active involvement of an adult supervisor in the treatment. For the purpose of speech therapy and administration of medication in the airways, alternative embodiments of the invention are provided according the previous descriptions. These aspects of the disclosure are important for a positive relation to be established between the young patient and the device and the adult supervisor or practitioner when he is present, and thereby increases the compliance and efficacy. In conclusion, this invention is more user-friendly and reaches significantly better results compared to the already known technical solutions for treatment of otitis, sinusitis, sudden atmospheric pressure change, speech therapy and administration of medication in the airways for inhalation.

Example 1

A pilot study conducted on thirty-four subjects with otitis media with effusion (OME) demonstrated 100% compliance and immediate improvement of the pressure of the middle ear after 2 minutes of usage. The subjects, aged 2-4 years, were recruited from a nursery school. The effect of middle ear ventilation was achieved in 91% of the ears.

Example 2

A pilot study conducted on six adults with symptoms of sinus and or ear squeeze at flights revealed immediate symptom relief in five of six (83%) of the subjects with no adverse effect observed.

Example 3

Studies on compliance of the device on children reveal that children form the age of 4 months may adapt to the present invention given the active involvement of the adult supervisor in the treatment.

Example 4

In a study including ten adult patients with chronic OME, all where able to use the device and achieve bilateral middle ear ventilation.

Example 5

Another study compared children with asthma, aged one to seven years for treatment with the new device compared to regular air chambers. The compliance, adaptation, ease of use and efficiency were compared. The compliance for using regular air chambers voluntarily was 67% whilst the new device revealed a compliance of 92% thanks to the parental aid, demonstration and instructions. The propagation of the medication throughout the children's airways was significantly higher with the new device thanks to the reservoir for drug accumulation, parental expiration into the system and gradual release at inhalation by the child. This allowed for a 40% reduction in the quantity of medication administrated as compared to regular air chambers.

CONCLUSION

The results above show an outstanding effect of the invented device compared with prior art. There are no former inventions adapted to treat all the referred conditions in young children.

The present invention combines efficiency with comfort and compliance for treatment at home or hospital for children. Subjective and objective measurements indicate both enhanced compliance and efficiency in the targeted conditions for children and adults using the present invention.

The invention claimed is:

1. A device for speech therapy, administration of inhalation medication and for treatment of otitis, sinusitis and barotrauma, the device comprising a patient interface adapted to cover at least a mouth and a nose of a patient and a visual and/or audio feedback mechanism which is connected to the patient interface via an internal air pressure in a compartment of the device, the compartment being adapted to be in fluid communication with the patient mouth and nose during operation of the device, the visual and/or audio feedback mechanism being adapted to be in fluid communication with the patient interface via the compartment, wherein the device comprises a supervisor interface adapted to cover at least a mouth and/or a nose of a supervisor and wherein the compartment is adapted to be in fluid communication with the supervisor mouth and nose, during operation of the device.

2. The device according to claim 1, wherein the device comprises a body having an inner surface defining the compartment with
- a first opening in communication with the compartment where the patient interface is connected to the first opening,
- a second opening in communication with the compartment where the visual and/or the audio feedback mechanism is connected to the second opening,
- a third opening in communication with the compartment where the supervisor interface is connected to the third opening, and
- the first opening and the third opening are arranged at a distance from each other and are arranged at opposite ends of the body in the longitudinal direction of the body,
- the second opening is positioned between the first opening and the third opening in the longitudinal direction of the body,
- the supervisor interface is arranged in a mirrored relationship relative to the patient interface.

3. The device according to claim 1, wherein the device comprises a one-way valve positioned between the supervisor interface and the visual and/or audio feedback mechanism for allowing air passage only in a direction from the supervisor interface towards the visual and/or audio feedback mechanism.

4. The device according to claim 1, wherein the device comprises a one-way valve associated with the supervisor interface for communication with ambient air for allowing air passage only in a direction to the supervisor interface.

5. The device according to claim 1, wherein the supervisor interface comprises a supervisor facemask.

6. The device according to claim 1, wherein the supervisor interface is adapted to be held in position by straps.

7. The device according to claim 1, wherein a filter is incorporated downstream of the supervisor interface.

8. The device according to claim 1, wherein the device comprises a one-way valve positioned between the patient interface and the visual and/or audio feedback mechanism for allowing air passage only in a direction from the patient interface towards the visual and/or audio feedback mechanism.

9. The device according to claim 1, wherein the device comprises a one-way valve associated to the patient interface for communication with ambient air for allowing air passage only in a direction to the patient interface.

10. The device according to claim 1, wherein the patient interface comprises a patient facemask is adapted to be held in position by straps and a filter is incorporated downstream of the supervisor interface.

11. The device according to claim 1, wherein the visual and/or audio feedback mechanism comprises a liquid-filled chamber.

12. The device according to any preceding claim 1, wherein the supervisor interface comprises a facemask, the patient interface comprises a facemask and wherein there are more than two facemasks connected to a connecting tube for group therapy.

13. The device according to claim 1, wherein the device comprises an air flow resistance means for providing a counter pressure in the compartment during operation of the device arranged at the second opening.

14. The device according to claim 1, wherein the device comprises a security valve in communication with the compartment for releasing air from the compartment if the internal pressure reaches a predefined threshold.

15. The device according to claim 1, wherein the device further comprises an additional opening in communication with the compartment.

* * * * *